US007427298B1

(12) United States Patent
Swanson, Sr.

(10) Patent No.: US 7,427,298 B1
(45) Date of Patent: Sep. 23, 2008

(54) PROSTHETIC SOCKET LOCK VALVE

(75) Inventor: Verner M. Swanson, Sr., Temperance, MI (US)

(73) Assignee: Bionix Prosthetic Solutions, LLC, Toledo, OH (US)

(*) Notice: Subject to any disclaimer, the term of this patent is extended or adjusted under 35 U.S.C. 154(b) by 180 days.

(21) Appl. No.: 11/346,030

(22) Filed: Feb. 2, 2006

Related U.S. Application Data

(60) Provisional application No. 60/649,156, filed on Feb. 2, 2005.

(51) Int. Cl.
*A61F 2/80* (2006.01)
(52) U.S. Cl. ........................................................ 623/34
(58) Field of Classification Search ............... 623/32–37
See application file for complete search history.

(56) References Cited

U.S. PATENT DOCUMENTS 6,334,876 B1 * 1/2002 Perkins .......................... 623/34

* cited by examiner

*Primary Examiner*—Bruce E. Snow
(74) *Attorney, Agent, or Firm*—Marshall & Melhorn, LLC

(57) ABSTRACT

A lock valve is provided on a conventional, mechanical lock member to add additional suspension by negative pressure in the socket created because of the intimate fit of the socket. The lock valve has a valve biased to a first position where the valve does not permit the ingress of air. When the valve is urged away from the first position to a second position, such as by pressing the lock valve inward toward the lock assembly, the mechanical locking member is released and the lock valve is opened to permit the ingress of air. As a result, the mechanical locking member and the negative pressure are simultaneously released.

15 Claims, 9 Drawing Sheets

PROSTHETIC SOCKET LOCK VALVE

RELATED APPLICATION

This application is claiming the benefit, under 35 U.S.C. § 119(e), of the provisional application filed Feb. 2, 2005 under 35 U.S.C. § 111 (b), which was granted Ser. No. 60/649,156. This provisional application is hereby incorporated by reference in its entirety.

BACKGROUND OF THE INVENTION

The invention relates to prosthetic devices and, in particular, to a lock valve for a prosthetic leg assembly.

The lock mechanisms that are the subject of the invention are commonly used to connect a residual limb socket to a prosthetic limb, such as knee joint, as an example. Such a prosthetic limb is conventionally secured to an amputee's residual limb stump by securing the prosthetic limb to a rigid socket. This may commonly be done through the use of a locking pin. In this technique, the amputee first dons a sock-like liner formed of an elastomer and optionally including a fabric cover. The lower or distal end of the liner is formed of a rigid material, such as urethane, and the locking pin extends from this rigid bottom. These liners are well known in the art. The pin is extended through the wall of the socket and a distal adapter mounted within or outside of the socket, and can be locked onto the lock mechanism mounted to the prosthetic limb to secure the prosthesis. Typically, the lock pin can be released only by moving a pinion gear in a direction parallel to its rotational axis until it disengages from the lock pin, e.g., via a manual release button.

BRIEF SUMMARY OF THE INVENTION

In accordance with the invention, a lock valve is provided on a conventional, mechanical lock member to add additional suspension by negative pressure in the socket created because of the intimate fit of the socket. The lock valve comprises a valve biased to a first position where the valve does not permit the ingress of air. When the valve is urged away from the first position to a second position, such as by pressing the lock valve inward toward the lock assembly, the mechanical locking member is released and the lock valve is opened to permit the ingress of air. As a result, the mechanical locking member and the negative pressure are simultaneously released.

BRIEF DESCRIPTION OF THE DRAWINGS

The advantages of the invention will become readily apparent to those skilled in the art from the following detailed description of a preferred embodiment when considered in the light of the accompanying drawings, in which.

DETAILED DESCRIPTION OF THE INVENTION

In accordance with the invention, a lock valve is added to a mechanical lock mechanism to add additional suspension by negative pressure in the socket created because of the intimate fit of the socket. Thus, in one aspect, the invention allows the conversion of a conventional non-suction lock to a suction lock, by providing a suction button or lock valve to take the place of the existing button, thereby providing suction if the remainder of the socket is fabricated in an air-tight manner.

Figure 1:
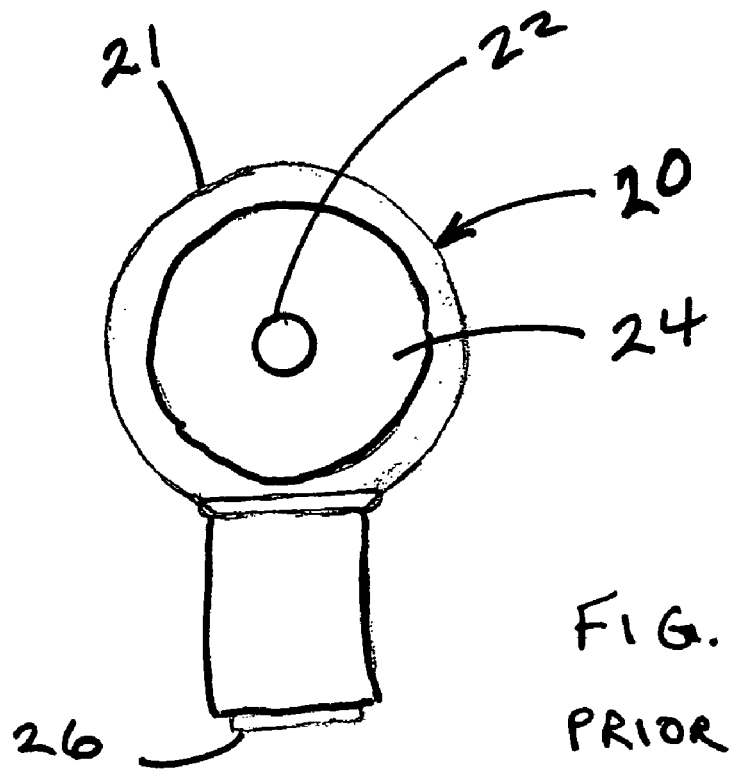
FIG. 1 is an end view of a conventional lock.
Figure 2:
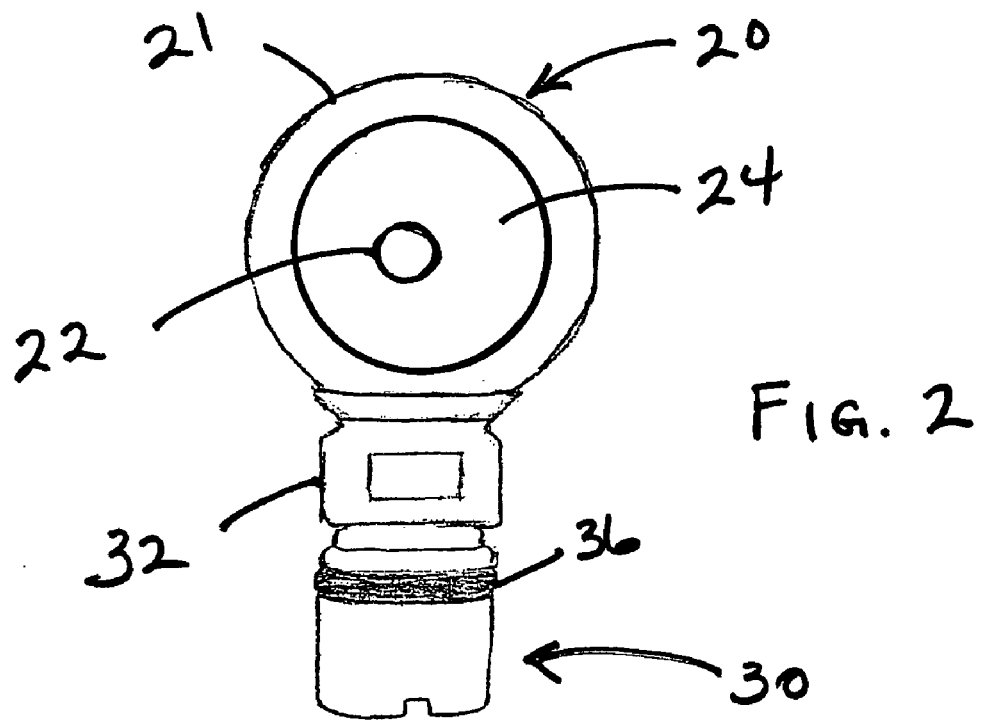
FIG. 2 is an end view of a lock including the valve assembly of the invention.

In the conventional lock, denoted generally at 20 in FIG. 1, the lock body 21 is provided with a centrally located bore 22 for receiving a mechanical locking member, typically a locking pin. A generally cup-shaped guide portion 24 may be provided to guide the end of the locking member into the bore 22.

Typically, the pin has a longitudinal series of rack-like serrations. The teeth of a pinion gear (not shown in FIG. 1) in the lock body extend into the bore 22 to engage the teeth of the locking pin found therein. The pinion gear is mounted for one way rotation to permit entry of the locking pin into the bore, but mechanically lock the lock pin against removal. The lock pin can be released only by moving the pinion gear in a direction parallel to its rotational axis until it disengages from the locking pin, e.g., via a manual release button 26.

In accordance with the invention, the lock assembly is provided with a lock valve 30 in place of the manual release button 26 that is conventional. Thus, the manual release button 26 may be removed from the lock body 21 (typically from a threaded nipple, not shown) and a connector sleeve 32 mounted in its place. A plastic valve dummy, such as the valve dummy 34 illustrated in FIG. 3, may then be threaded onto the connector sleeve 32, where it remains during fabrication of the prosthetic socket. Such fabrication is well known to those skilled in the art. Following fabrication of the socket, the dummy 34 is removed and the lock valve 30 is threaded onto the sleeve secured to the lock body 21. An annular seal 36 is preferably provided between annular surfaces on the lock valve 30 and the connector sleeve 32 to provide an air-tight seal therebetween.

The lock valve 30 may preferably be an expulsion type valve that, while in the non-actuated position, allows only the egress of air from the lock and socket (e.g. during donning). Then, when in the actuated (depressed) position, it allows the ingress of air into the lock and socket (facilitating removal). The lock valve may also be designed to prevent any egress of air from the lock and socket, and only to allow the ingress of air when actuated.

Figure 3:
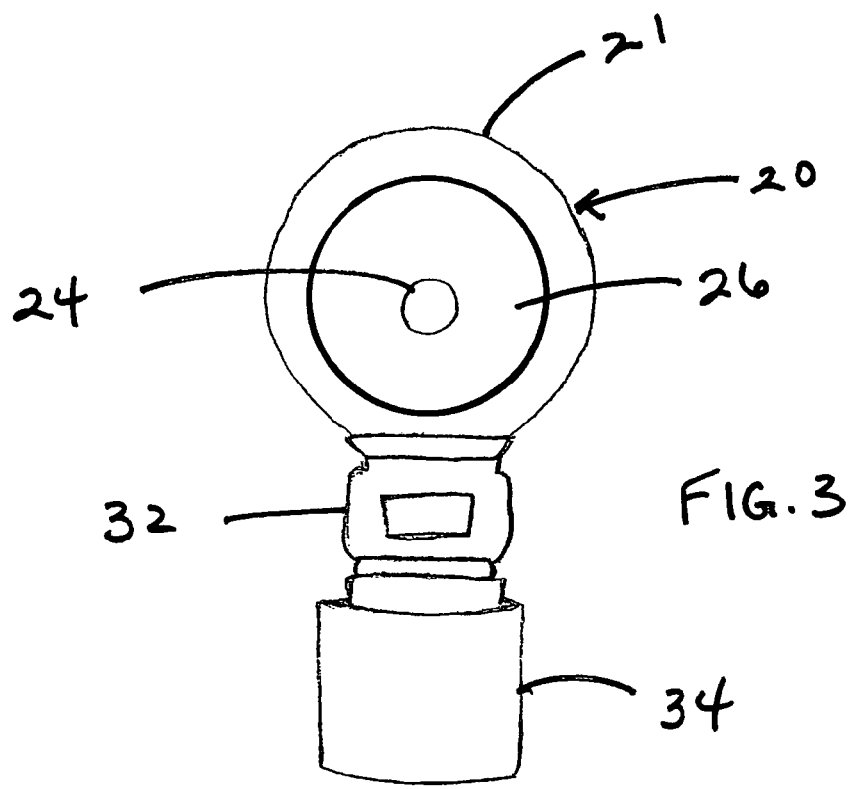
FIG. 3 is an end view of a lock including a valve of the invention assembled with a fabrication valve dummy.
Figure 4:
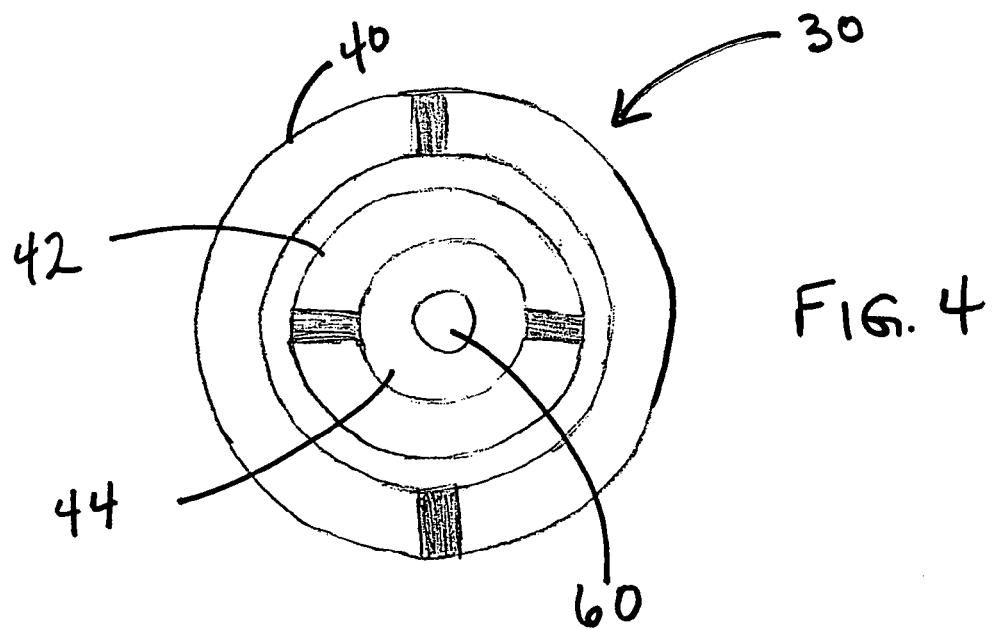
FIG. 4 is an enlarged side view of an embodiment of the lock valve of the invention.

In an alternate embodiment, the assembly may be fabricated by threading a valve dummy, like the dummy 34 shown in FIG. 3, directly onto the nipple (without a connector sleeve) after the manual release button 26 has been removed from the threaded nipple. The valve dummy remains there during fabrication of the prosthetic socket. As with the dummy 34, the dummy includes a shoulder adapted to form a corresponding shoulder in the plastic socket during fabrication. Following fabrication of the socket, the dummy is removed and a lock valve is threaded onto the nipple. Such a preferred embodiment of the lock valve 38 is shown in more detail in FIGS. 4 and 5. The lock valve 38 is an adjustable, one-way leak rate valve.

The lock valve 38 includes the main valve body 40 in which is mounted an inner member 42, which in turn accepts the valve 44, and is connected to the threaded nipple 46 via a smaller diameter connector portion 47. The threaded nipple 46 is secured to the lock body 20. Such an assembly allows for ready access to the lock mechanism, and allows actuation of the valve 44 simultaneously with release of the mechanical lock mechanism as the valve 44 urges the pinion gear member 48 in the lock body 20 out of the bore 22 to disengage the teeth of the locking pin found therein.

Figure 5:
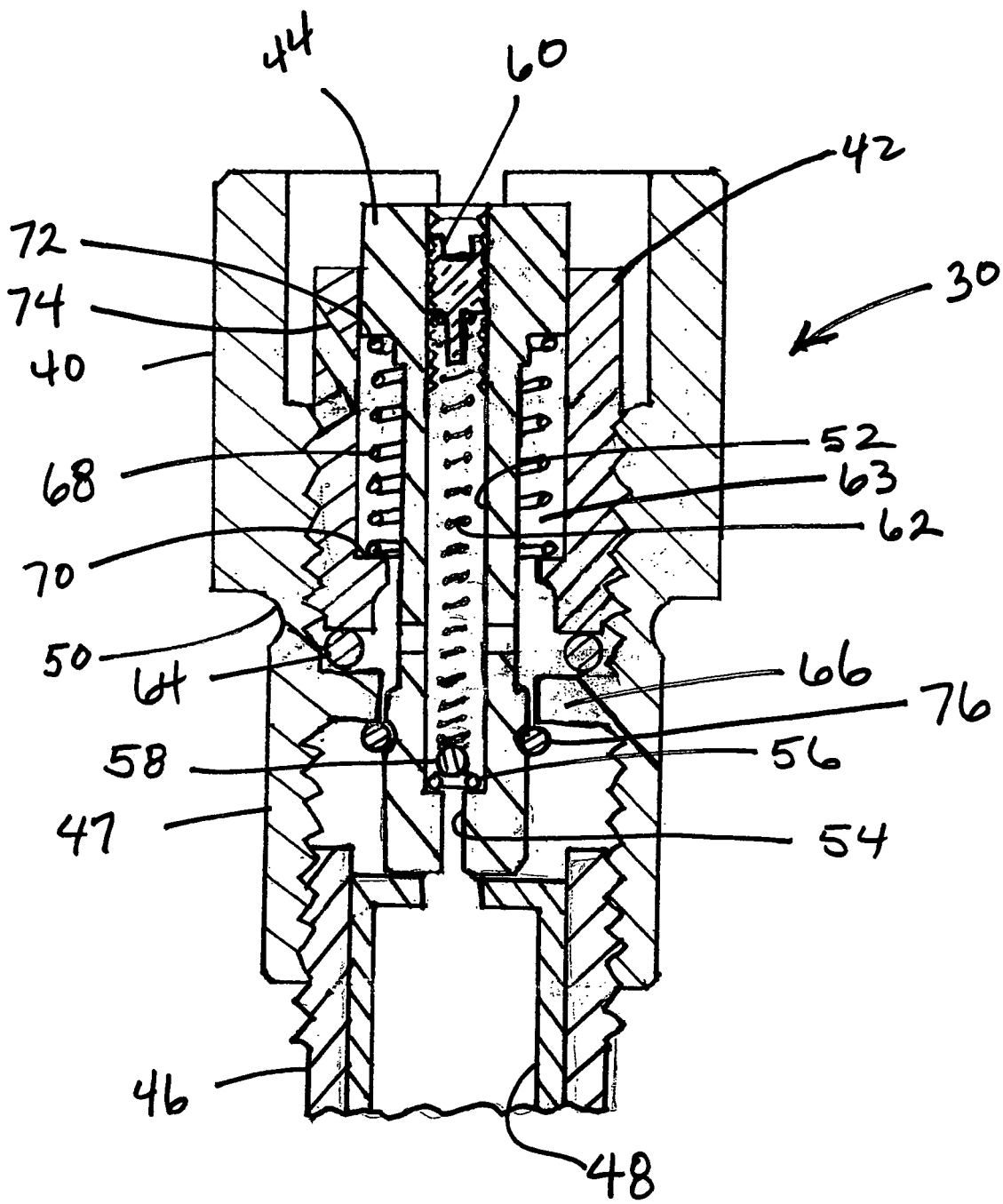
FIG. 5 is an enlarged, cross-sectional view of the lock valve of FIG. 4.

FIG. 5 is a cross-sectional view illustrating a preferred embodiment of the lock valve 30 in greater detail. The valve body 40 includes an annular groove 50 at the connector portion 47 for receiving the annular seal 36 added to provide an air-tight seal between annular surfaces on the lock valve 30 and the surface of the socket (not shown in FIG. 5).

The valve 44 includes a larger diameter central bore 52 aligned with a smaller diameter central bore 54. An annular seal 56 is positioned on the shoulder formed where the two meet, and valve ball 58 rests on the annular seal 56. A set screw or valve needle 60 is mounted in the upper portion of the larger diameter central bore 52, with a biasing means, such as the spring 62, extends between the valve needle 60 and the valve ball 58, urging the same against the annular seal 56. The valve needle 60 is preferably adjustable, such as by means of a threaded connection within the bore 52, to allow for variation in the force exerted against the ball 58. This allows for adjustment of the pressure required to allow the egress of air through the valve 44, for example during donning. One or more air release ports provide communication between the bore 52 and a space 63 defined by the outer surface of the valve 44, the inner member 42 and an annular seal 64 between the inner end of the inner member 42 and an inwardly extending annular flange 66 on the lock body 40.

The valve 44 rests within the inner member 42, which is in turn secured within the lock body 40, such as by the mating threads illustrated in FIG. 5. A biasing means, such as the spring 68, extends between an inwardly extending annular shoulder 70 on the inner member 42 and an outwardly extending annular shoulder 72 on the valve 44. The spring 68 normally keeps the valve 44 in the non-actuated position. The inner member 42 is further provided with at least one air release port 74 that provides communication between the space 63 and the exterior of the lock valve 30.

The end of the valve 44 extending beyond the flange 66 is provided with an annular release seal 76 seated in an annular groove formed in the valve 44. The release seal 76 is normally urged upward (as shown in FIG. 5) against an annular surface of the flange 66 to form a seal therewith. When the valve 44 is depressed, or forced downward as shown in FIG. 5, the end of the valve 44 engages the mechanical locking member 48, which is thereby disengaged from the locking pin. At the same time, the annular release seal 56 is moved away from the flange 66, allow air to egress from the socket and lock assembly, around the valve 44 and out the 74 air release port 74 to the exterior of the lock valve 30.

Figure 6:
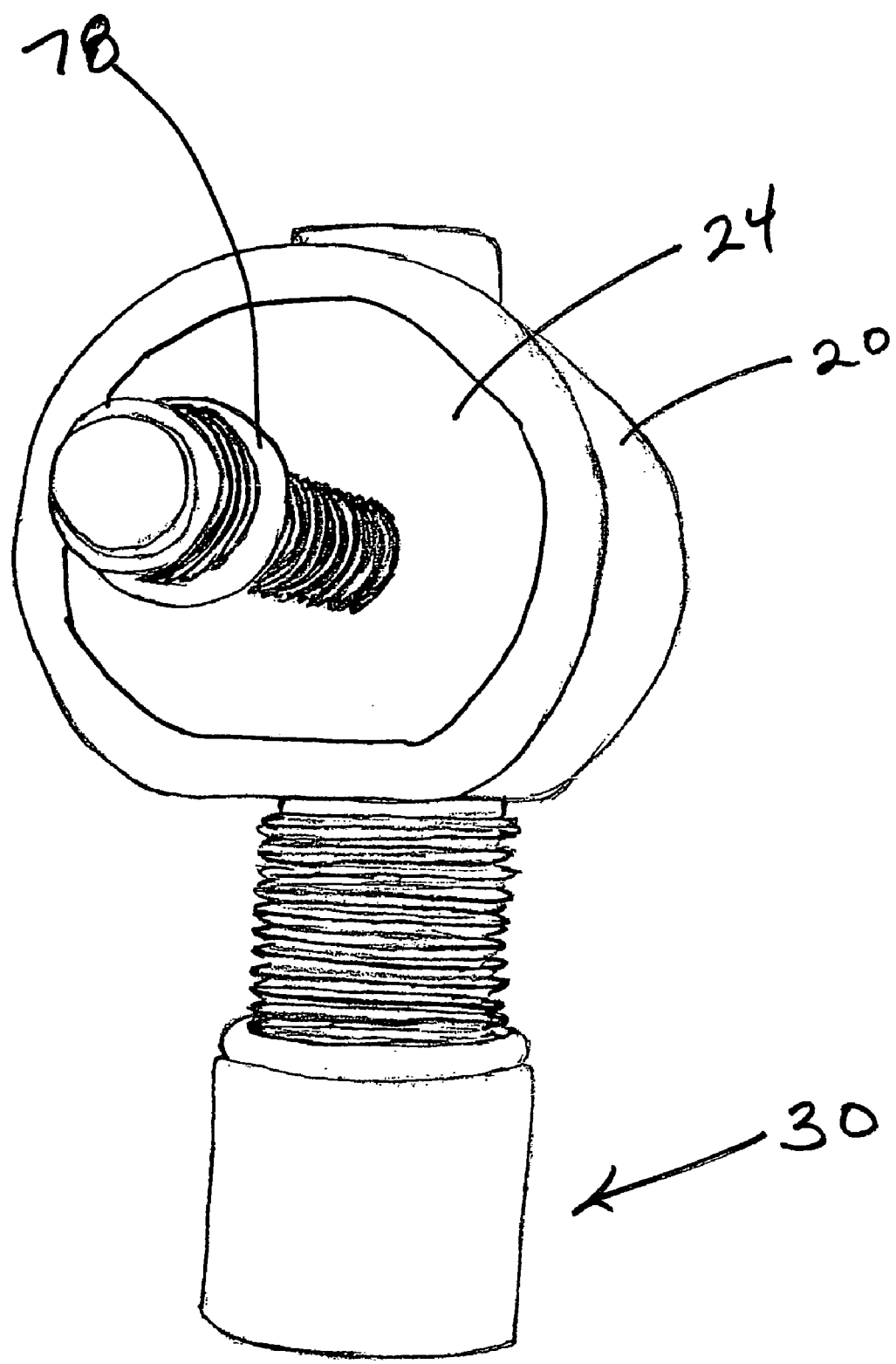
FIG. 6 is a top perspective view of a lock with a locking pin and a lock valve in accordance with the invention.
Figure 7:
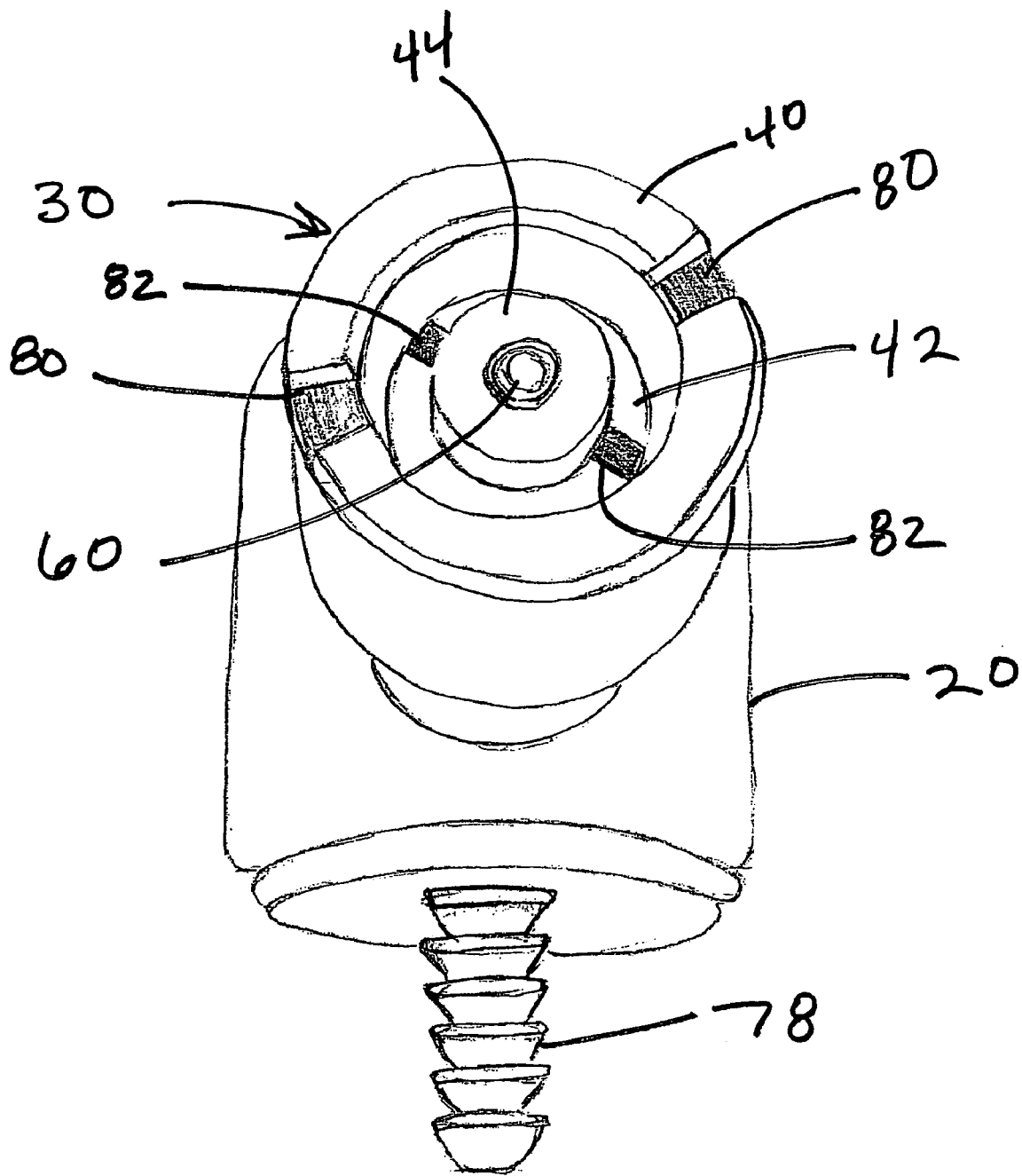
FIG. 7 is a bottom perspective view of the lock, locking pin and lock valve shown in FIG. 6.

FIG. 6 illustrates the lock 20 and lock valve 30 of the invention with a locking pin 78 received in the lock bore 22. For ease of illustration, the locking pin 78 has been shown in FIG. 6 without the liner with which it would be formed. FIG. 7 is a view of the assembly of FIG. 6 from a different perspective. This view shows the opposing pair of notches 80 that may be formed in the upper edges of the valve body 40 to facilitate attachment and removal of the lock valve 30 to the lock 20, and the similar pair of notches 82 that may be formed in the upper edges of the inner member 42 to facilitate assembly and disassembly of the lock valve itself.

Figure 8:
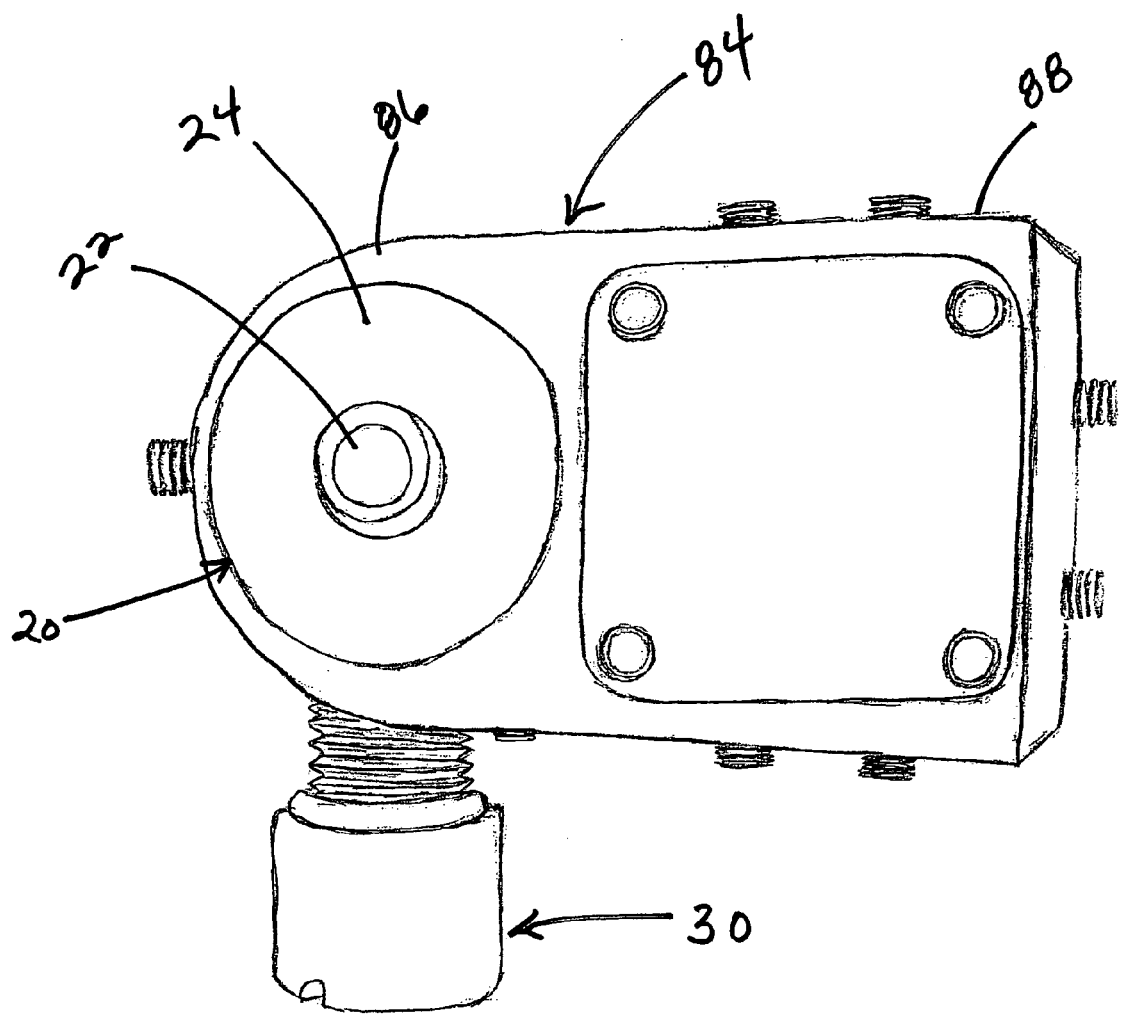
FIG. 8 is a top view of a lock with a locking pin and a lock valve in accordance with the invention assembled with a socket adapter bracket.
Figure 9:
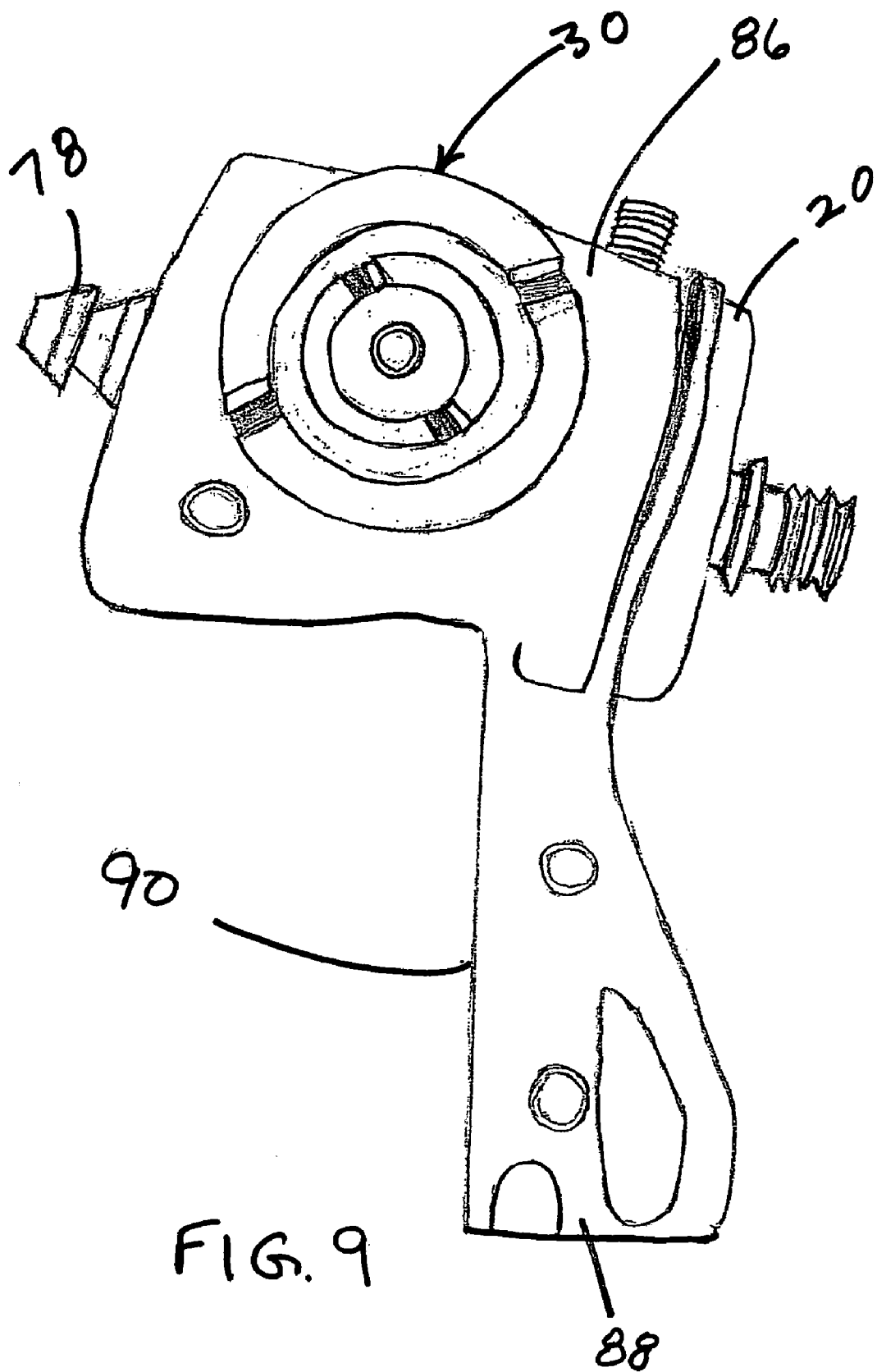
FIG. 9 is a side view of the lock, lock valve and socket adapter bracket shown in FIG. 8.

FIGS. 8 and 9 show the lock 20, lock valve 30 and locking pin 78 illustrated in FIGS. 6 and 7 as mounted to a flexion length offset adapter bracket assembly 84 as disclosed in U.S. Pat. No. 6,905,519, which is incorporated by reference herein in its entirety. The lock 20 is secured at the first end 86 of the bracket 84, the lock being adapted to releasably engage the locking pin 78 of the liner (not shown). The second end 88 of the bracket 84 includes a mounting face 90 (FIG. 9) adapted to have the prosthetic limb mounted thereto in such a manner that the longitudinal axis of the prosthetic limb is spaced apart from the longitudinal axis of the locking pin of the liner and, depending upon the shape of the bracket, may be angled relative thereto. Set screws 92 may be secured to the bracket to facilitate attachment of the thermoplastic to the bracket upon fabrication of the socket about the lock assembly.

Figure 10:
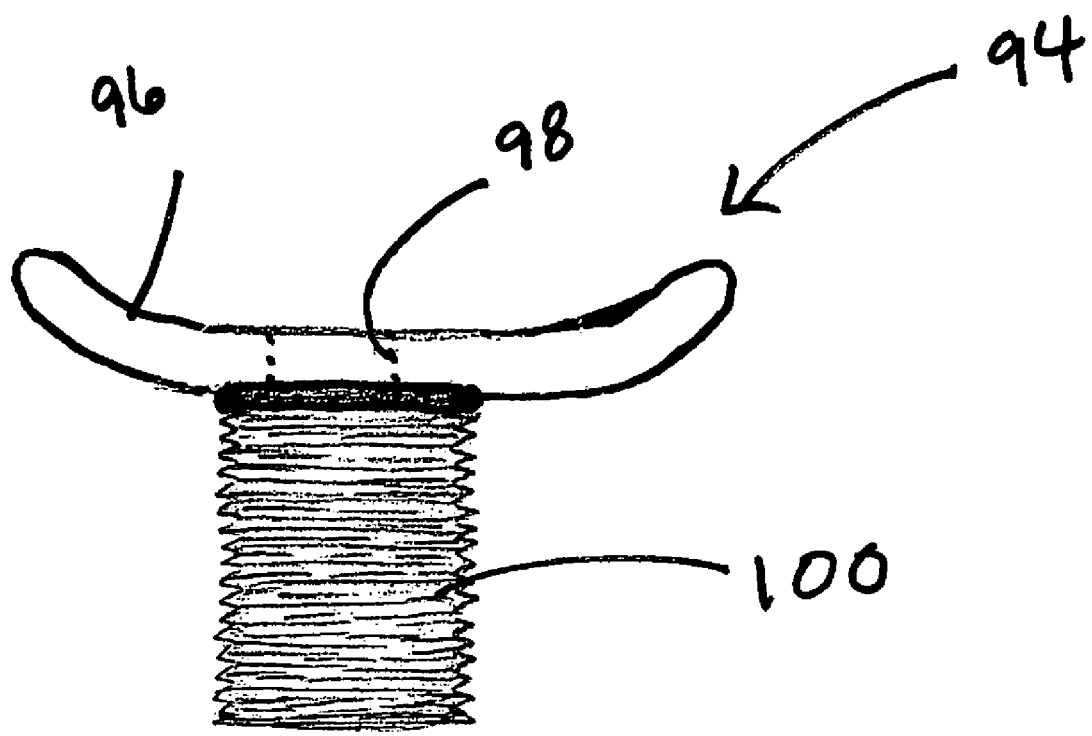
FIG. 10 is a side view of a lock seal adapter for use in connection with an embodiment of the invention.
Figure 11:
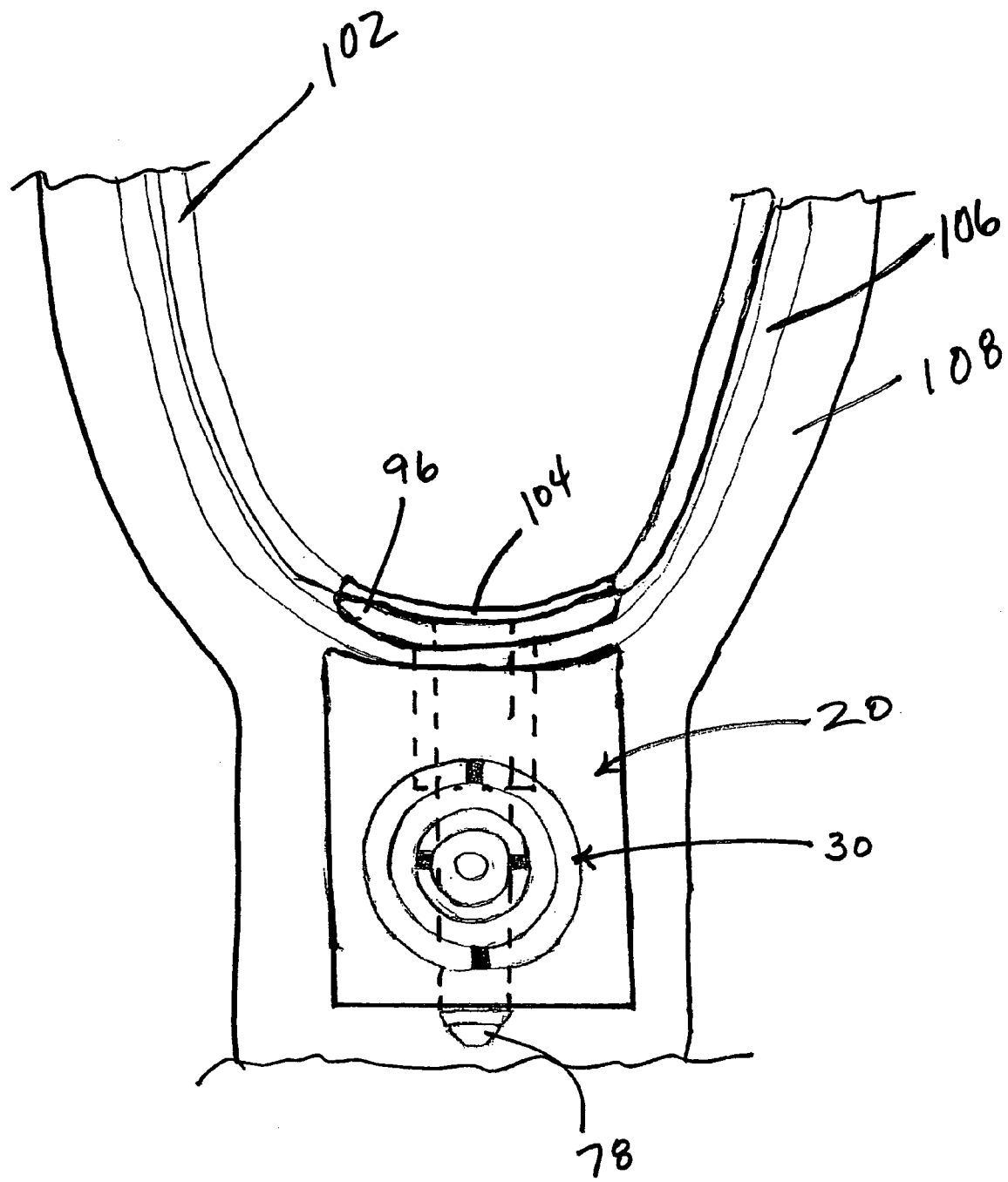
FIG. 11 is a somewhat schematic side view, with portions broken away, of a prosthetic leg assembly including a lock, lock valve, and lock seal adapter in accordance with the invention.

In another aspect of the invention, a lock seal adaptor, denoted as numeral 94 in FIGS. 10 and 11, may be provided. The lock seal adaptor 94 includes a generally cup-shaped portion 96 having a central aperture 98 therein for receiving a locking pin 78. A hollow, threaded sleeve 100 extends from the cup-shaped portion 96. The lock seal adaptor 94 may be secured to a lock 20, having the lock valve 30 of the invention mounted thereto, with an annular seal 101.

A residual limb liner 102 includes a rigid, cup-shaped bottom portion 104 from which the locking pin 78 extends. An inner flexible socket 106 is also provided that includes an aperture through which the locking pin 78 and 100 sleeve extend, with a portion of the inner flexible socket 106 about this aperture being sandwiched between the bottom surface of the cup-shaped portion 96 of the adaptor 94 and the top surface of the lock 20. A seal is thus created between the lower surface of the cup-shaped portion 96 and the top surface of the lock 20. A rigid laminated or thermoplastic outer socket or frame 108 is formed about the lock 20 and the lock seal adaptor 94, with the inner flexible socket 106 and liner 102 fitting within the outer socket 106.

The lock seal adaptor 94 in accordance with this aspect of the invention provides a seal that allows for openings to be made in the rigid outer socket 108 without a loss of negative pressure. In some instances, such openings in the outer socket 108 may be desirable, for example to relieve localized pressure on the patient's residual limb.

In accordance with the provisions of the patent statutes, the invention has been described in what is considered to represent its preferred embodiments. However, it should be noted that the invention could be practiced otherwise than as specifically illustrated and described without departing from its spirit or scope. For example, the lock valve may be secured to lock by internal or external threads depending on the particular lock, and may even be secured by attachment means other than a threaded connection.

This lock valve may be adapted to any lock mechanism that has horizontal side-to-side travel via actuation of a lock type button. In doing so, the valve lock many be designed for various mechanical lock mechanisms.

The lock valve may be originally fabricated within the thermoplastic or thermosetting socket (laminated) by incorporating the lock valve housing within the socket. The lock valve may be retrofit into a socket if the lock valve housing was incorporated into the construction of the socket. The lock valve may be designed with any lock mechanism to add suction suspension capability along with the mechanical lock type suspension. The mechanical lock mechanism will suspend the prosthesis with the mechanical lock device. There is an inherent amount of pistoning (in and out travel) of the stump due to the limitations of the mechanical lock mechanism and or the material stretching of the roll-on suction liner. The addition of the lock valve helps minimize that inherent pistoning.

There are currently a number of commercially available lock mechanisms and commercially available suction valves on the market. This invention combines the ability to have both an airtight seal over the lock mechanism with either an adjustable setscrew for automatic one-way air expulsion or a non-adjustable valve over the lock mechanism. The lock mechanism suspension may therefore be upgraded with the addition of the lock valve for suction suspension.

The lock valve may be easily replaced if service is needed, and provides the patient with additional options. For example, if the patient didn't like the feel of suction, the lock valve could be removed from the lock mechanism. Upon removal of the lock valve, the lock mechanism would provide mechanical suspension only.

What is claimed is:

1. A lock assembly for selectively connecting a residual limb liner having a mechanical locking member to a prosthetic limb, the lock assembly comprising a lock valve having a valve biased to a first position where said valve does not permit the ingress of air, and whereby when said valve is urged away from said first position to a second position, the mechanical locking member is released and said valve is opened to permit the ingress of air, and wherein said valve is an expulsion type valve that, while in said first position, allows only the egress of air through the valve from the lock.

2. The lock assembly of claim 1, wherein said valve is adjustable, to allow for variation in the pressure required to allow the egress of air through the valve.

3. The lock assembly of claim 1, further comprising a pinion gear member mounted in the lock and adapted to selectively engage and disengage the teeth of a locking pin.

4. The lock assembly of claim 1, further comprising a spring biasing said valve to said first position.

5. The lock assembly of claim 1, wherein the valve is translatable from the first position to the second position.

6. The lock assembly of claim 1, wherein the lock valve comprises a main valve body in which is mounted an inner member, which in turn accepts the valve.

7. The lock assembly of claim 6, wherein the inner member comprises at least one air release port that provides communication between an inner space defined between the valve and the inner member and the exterior of the lock valve.

8. A prosthetic device comprising:
a residual limb socket having a sleeve, an open end adapted to receive a residual limb and a closed end having a through-hole formed therein for receiving a residual limb liner locking pin;
a lock secured to the closed end of the socket, the lock being adapted to releasably engage the locking pin of the liner with a mechanical locking member, the lock comprising a lock valve biased to a first position where said lock valve does not permit the ingress of air, and whereby when said lock valve is urged away from said first position to a second position, the mechanical locking member is released and said lock valve is opened to permit the ingress of air, and wherein said valve is an expulsion type valve that, while in said first position, allows only the egress of air through the valve from the lock.

9. The prosthetic device of claim 8, further comprising a prosthetic limb secured to the lock.

10. The prosthetic device of claim 8, wherein said valve is adjustable, to allow for variation in the pressure required to allow the egress of air through the valve.

11. The prosthetic device of claim 8, further comprising a spring biasing said valve to said first position.

12. The prosthetic device of claim 8, wherein the valve is translatable from the first position to the second position.

13. The prosthetic device of claim 8, wherein the lock valve comprises a main valve body in which is mounted an inner member, which in turn accepts the valve.

14. The prosthetic device of claim 8, further comprising an offset adapter bracket assembly having a first end to which the lock is secured and a second end to which the prosthetic limb is mounted such that the longitudinal axis of the prosthetic limb is spaced apart from the longitudinal axis of the locking pin of the liner.

15. A lock assembly for selectively connecting a residual limb liner having a locking pin to a prosthetic limb, the lock assembly comprising a lock having a lock valve biased to a first position where said lock valve does not permit the ingress of air, and whereby when said lock valve is urged away from said first position to a second position, the locking pin is released and said lock valve is opened to permit the ingress of air, and a lock seal adaptor secured to the lock, the lock seal adaptor comprising a generally cup-shaped portion having a central aperture therein for receiving the locking pin, and a hollow, threaded sleeve extending from the cup-shaped portion.

* * * * *